United States Patent
Xie et al.

(10) Patent No.: US 9,410,081 B2
(45) Date of Patent: Aug. 9, 2016

(54) LUMINESCENT MATERIALS

(71) Applicant: EAST CHINA UNIVERSITY OF SCIENCE AND TECHNOLOGY, Shanghai (CN)

(72) Inventors: Yongshu Xie, Shanghai (CN); Bin Chen, Shanghai (CN); Cheng Wang, Shanghai (CN); Yubin Ding, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 14/435,842

(22) PCT Filed: Oct. 15, 2012

(86) PCT No.: PCT/CN2012/082984
§ 371 (c)(1),
(2) Date: Apr. 15, 2015

(87) PCT Pub. No.: WO2014/059586
PCT Pub. Date: Apr. 24, 2014

(65) Prior Publication Data
US 2015/0329773 A1   Nov. 19, 2015

(51) Int. Cl.
C09K 11/06 (2006.01)
C07D 401/12 (2006.01)
H01L 51/00 (2006.01)
H05B 33/14 (2006.01)
C07D 213/74 (2006.01)
H01L 51/50 (2006.01)

(52) U.S. Cl.
CPC .............. C09K 11/06 (2013.01); C07D 213/74 (2013.01); C07D 401/12 (2013.01); H01L 51/006 (2013.01); H01L 51/0052 (2013.01); H01L 51/0058 (2013.01); H01L 51/0061 (2013.01); H01L 51/0067 (2013.01); H01L 51/0071 (2013.01); H05B 33/14 (2013.01); C09K 2211/1007 (2013.01); C09K 2211/1011 (2013.01); C09K 2211/1022 (2013.01); C09K 2211/1029 (2013.01); H01L 51/0059 (2013.01); H01L 51/5012 (2013.01); H01L 51/5056 (2013.01); H01L 51/5072 (2013.01); H01L 51/5096 (2013.01)

(58) Field of Classification Search
None
See application file for complete search history.

(56) References Cited

U.S. PATENT DOCUMENTS 8,653,230 B2   2/2014   Xie

FOREIGN PATENT DOCUMENTS

| JP | 2011111433 A | 6/2011 |
| WO | WO2004078872 A2 | 9/2004 |
| WO | WO2011085951 A1 | 7/2011 |

OTHER PUBLICATIONS

International Search Report and Written Opinion for PCT/CN2012/082984 dated Jul. 18, 2013.
Diao et al., Synthesis and photophysical processes of an anthracene derivative containing hole transfer groups, *Spectrochimica Acta Part A: Molecular and Biomolecular Spectroscopy* (Jan. 2011), 78(1):294-297.
Ding et al., Selective and sensitive "turn-on" fluorescent Zn2+ sensors based on di- and tripyrrins with readily modulated emission wavelengths, *Chem. Communications* (2011), 47(19):5431-5433.
Gan et al., 1,8-Naphthalimides for non-doping OLEDs: the tunable emission color from blue, green to red, *Journal of Photochemistry and Photobiology A: Chemistry* (2004), 162:399-406.
Huang et al., A colorimetric and fluorescent turn-on sensor for pyrophosphate anion based on a dicyanomethylene-4H-chromene framework, *Chemical Communications* (2008), 41:5143-5145.
Shavaleev et al., New ligands in the 2,20-dipyridylamine series and their Re(I) complexes; synthesis, structures and luminescence properties, *New J. Chem* (Feb. 12, 2004), 28:398-405.
Silva et al., 9-Anthrylmethyl)bis(2-pyridylmethyl)amine, *Acta Cryst* (Aug. 1998), 54(Part 8):1117-1119.

*Primary Examiner* — Timothy R Rozof
(74) *Attorney, Agent, or Firm* — Pepper Hamilton LLP

(57) ABSTRACT

The invention provides photoluminescent compounds, reactive intermediates used to synthesize photoluminescent compounds, and methods of synthesizing and using photoluminescent compounds, among others. The compounds comprise phenanthrene and dipyridylamine moieties. The compounds are colored and fluoresce upon excitation. Methods are included for using the compounds to detect metal ions by spectral changes of wavelength shift or a change in fluorescence intensity. Compositions in polymers and solvents are provided for use as a film, paint, reflective surfaces, and electroluminescent devices are provided.

24 Claims, 2 Drawing Sheets

LUMINESCENT MATERIALS

CROSS-REFERENCE TO RELATED APPLICATIONS

This application is a national phase application under 35 U.S.C. §371 of International Application No. PCT/CN2012/082984, filed Oct. 15, 2012 and entitled "NOVEL LUMINESCENT MATERIALS," the disclosure of which is incorporated by reference in its entirety and for all purposes.

Both anthracene and 2,2'-dipyridylamine (dpa) are highly efficient light emitting materials. It has been reported that the introduction of two dpa units to the 9 and 10 positions of anthracene by nitrogen-carbon bonds could afford a luminescent compound anthracene-(dpa)$_2$ as blue light-emitting materials. Modulation of the emission color is difficult with anthracene-(dpa)$_2$. It is desired to develop luminescent compounds with the emission colors easily modulated to afford full-color luminescence.

SUMMARY OF THE INVENTION

The invention provides photoluminescent compounds, reactive intermediates used to synthesize photoluminescent compounds, and methods of synthesizing and using photoluminescent compounds, among others.

The compounds relate generally to the following structure:

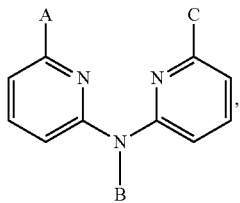

The embodiment has A as hydrogen or -L$_A$-R$^1$, B as hydrogen or -L$_B$-R$^1$, and C as hydrogen or L$_C$-R$^1$. In some embodiments, R$^1$ is

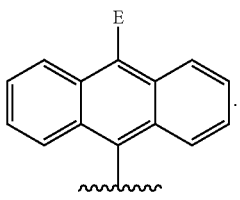

wherein E is a hydrogen, halogen, -G, —O-G, or NG$_2$, and wherein G is an aryl, substituted aryl, heteroaryl, substituted heteroaryl, or alkyl. Further, embodiments include those wherein -L$_A$-, -L$_B$-, and -L$_C$- are independently a bond or ethynyl, at least one of A, B and C is -L$_A$-R$^1$, -L$_B$-R$^1$, or -L$_C$-R$^1$, and if B is -L$_B$-R$^1$ and -L$_B$- is a bond, then E is hydrogen, G, or —O-G. Methods for preparation of the compounds are provided.

The compounds are colored and fluoresce upon excitation. Methods are included for using the compounds to detect metal ions by examination of changes to the spectrum. The spectral changes can be a wavelength shift or a change in fluorescence intensity. The change can occur upon addition of metal ions, and the change upon addition of metal ions can be reversed upon addition of metal chelators. The detection of ions may be provided for in a kit of the compound and other necessary articles.

Compositions of the compound in polymers and solvents for use as a film, paint, or reflective surface are provided. Further, the compounds can be used in electroluminescent devices including flat panel display devices.

The nature of the invention will be understood more readily after consideration of the drawing, chemical structures, and detailed description of the invention that follow.

DETAILED DESCRIPTION

Figure 1:
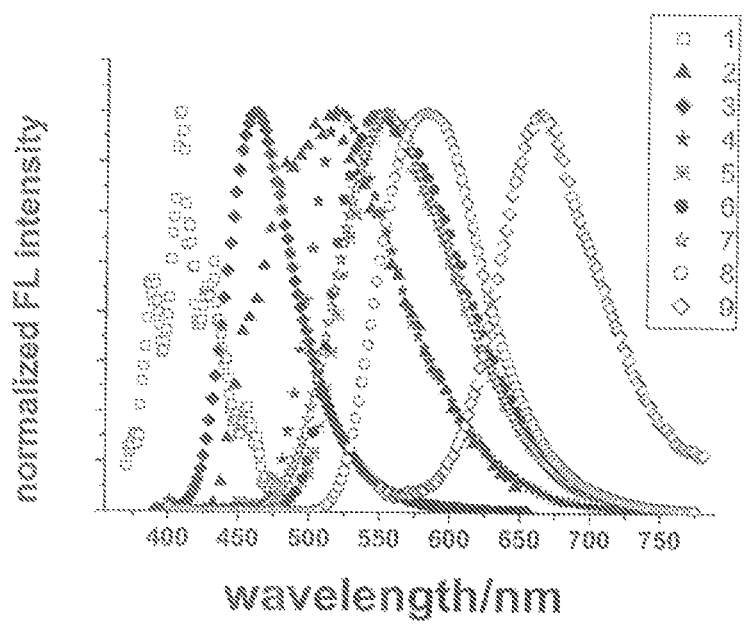
FIG. 1: Normalized photoluminescence spectra of compounds 1-9.

The above summary of the present invention is not intended to describe each illustrated embodiment or every possible implementation of the present invention. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, octyl, decyl, tetradecyl, hexadecyl, eicosyl, tetracosyl and the like. "Cycloalkyl" or "cycloalkyl groups" are branched or unbranched hydrocarbons in which all or some of the carbons are arranged in a ring, such as but not limited to cyclopentyl, cyclohexyl, methylcyclohexyl and the like. The term "lower alkyl" includes an alkyl group of 1 to 10 carbon atoms.

The term "aryl" or "aryl group" refers to monovalent aromatic hydrocarbon radicals or groups consisting of one or more fused rings in which at least one ring is aromatic in nature. Aryls may include but are not limited to phenyl, naphthyl, biphenyl ring systems and the like. The aryl group may be unsubstituted or substituted with a variety of substituents including, but not limited to, alkyl, alkenyl, halide, benzylic, alkyl or aromatic ether, nitro, cyano and the like and combinations thereof.

"Substituent" refers to a molecular group that replaces a hydrogen in a compound and may include, but are not limited to, trifluoromethyl, nitro, cyano, $C_1$-$C_{20}$ alkyl, aromatic or aryl, halide (F, Cl, Br, I), $C_1$-$C_{20}$ alkyl ether, benzyl halide, benzyl ether, aromatic or aryl ether, hydroxy, alkoxy, amino, alkylamino (—NHR'), dialkylamino (—NR'R") or other groups which do not interfere with the formation of the diaryl alkylphosphonate.

As defined herein, an "arylol" or an "arylol group" is an aryl group with a hydroxyl, OH, group substituent on the aryl ring. Non-limiting examples of an arylol are phenol, naphthalenol and the like. A wide variety of arylols may be used in the embodiments of the invention and are commercially available.

The term "alkanol" or "alkanol group" refers to a compound including an alkyl of 1 to 20 carbon atoms or more having at least one hydroxyl group substituent. Examples of alkanols include but are not limited to methanol, ethanol, 1- and 2-propanol, 1,1-dimethylethanol, hexanol, octanol and the like. Alkanol groups may be optionally substituted with substituents as described above.

The term "alkenol" or "alkenol group" refers to a compound including an alkene of 2 to 20 carbon atoms or more having at least one hydroxyl group substituent. The hydroxyl may be arranged in either isomeric configuration (cis or trans). Alkenols may be further substituted with one or more substituents as described above and may be used in place of alkanols in some embodiments of the invention. Alkenols are known to those skilled in the art and many are readily available commercially.

The term "organic polymer matrix" refers to an organic polymer or mixture of one or more organic polymers. An organic polymer comprises molecules in which at least one of the repeating units is an organic moiety which contains covalently bonded carbon atoms and optionally contains various other atoms. Typically an organic moiety contains a carbon-carbon bonded backbone or ring structure which may be substituted with various substituents (other than hydrogen) containing various atoms or in which the backbone remains predominantly composed of carbon, but may contain other atoms (e.g., O, S, N, etc.). Organic polymers may be formed having more than one repeat unit that are different in structure from each other, and are distributed along the polymer chain in any ordered or random arrangement or sequence. Therefore, the term polymer herein encompasses also random, alternated and block copolymers. Organic polymer matrices can include, but are not limited to, polyethylene, polypropylene, polystyrene, polycarbonate, acrylates, polymethyl methacrylate, hydroxyethyl acrylate, hexanediol diacrylate, neopentylglycol diacrylate, methyl-alpha-chloroacrylate, trimethylolpropane triacrylate, dipentaol hexaacrylate, trimethylol propane tridiethyleneglycol acrylate, urethane acrylate, adipic acid hexamethylenediamineoligomer, or synthetic polymers such as polytetrafluoroethylene, polyethylene terephthalate, polyparaxylene, trifluorochloroethylene, allyl trifluoroacetylene, combinations thereof, or the like.

An embodiment includes a compound of formula I:

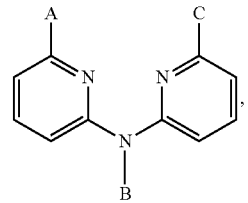

The embodiment has A as hydrogen or $-L_A-R^1$, B as hydrogen or $-L_B-R^1$, and C as hydrogen or $-L_C-R^1$. In some embodiments, $R^1$ is wherein E is a hydrogen, halogen, -G, —O-G, or $NG_2$, and wherein G is an aryl, substituted aryl, heteroaryl, substituted heteroaryl, or alkyl. Further, embodiments include those wherein $-L_A-$, $-L_B-$, and $-L_C-$ are independently a bond or ethynyl, at least one of A, B and C is $-L_A-R^1$, $-L_B-R^1$, or $-L_C-R^1$, and if B is $-L_B-R^1$ and $-L_B-$ is a bond, then E is hydrogen, G, or —O-G. Various embodiments include salts thereof.

In some embodiments of the compound, G is phenyl, substituted phenyl, biphenyl, substituted biphenyl, pyridyl, substituted pyridyl, naphthyl, substituted naphthyl, quinolyl, substituted quinolyl, isoquinolyl, substituted isoquinolyl, fluorenyl, substituted fluorenyl, terphenyl, substituted terphenyl, methyl, ethyl, propyl, isopropyl, or t-butyl. In other embodiments, G is aryl, substituted aryl or heteroaryl, substituted heteroaryl. In yet other embodiments, G is phenyl, substituted phenyl, biphenyl, substituted biphenyl, pyridyl, substituted pyridyl, naphthyl, substituted naphthyl, quinolyl, substituted quinolyl, isoquinolyl, substituted isoquinolyl, fluorenyl, substituted fluorenyl, or terphenyl, substituted terphenyl. In some embodiments, G is aryl or heteroaryl. In other embodiments, G is phenyl, biphenyl, pyridyl, naphthyl, quinolyl, isoquinolyl, fluorenyl, or terphenyl. In still other embodiments, G is aryl. G may be phenyl, biphenyl, naphthyl, fluorenyl, or terphenyl in embodiments. G may be heteroaryl in other embodiments. G may be pyridyl, quinolinyl or isoquinolinyl in still other embodiments. G may be phenyl, or substituted phenyl, in yet other embodiments. In some embodiments, G is phenyl. In other embodiments, G is pyridyl or substituted pyridyl. In still other embodiments, G is 2-pyridyl. In yet other embodiments, G is methyl, ethyl, propyl, isopropyl, or t-butyl.

In various embodiments of the compound, $-L_A-R^1$ and $-L_A-$ is a bond, B is hydrogen, and C is hydrogen. In other embodiments, B is $-L_B-R^1$ and $-L_B-$ is a bond, A is hydrogen, and C is hydrogen. In still other embodiments, A is $-L_A-R^1$ and $-L_A-$ is ethynyl, B is hydrogen, and C is hydrogen.

In various embodiments of the compound, the substitution on G is one or more of alkyl, aryl, alkoxy, alkylamino, halogen, aryloxy, arylamino, alkylsilyl, or arylsilyl. In other embodiments, substitution on G is methyl, ethyl, propyl, isopropyl, t-butyl, cyclohexyl, methoxy, ethoxy, propoxy, butoxy, dimethyl amino, trimethylsilyl, cyano, fluorine, chlorine, phenoxy, tolyloxy, dimethylamino, diethylamino, diphenylamino, or triphenylsilyl. In still other embodiments, substitution on G is t-butylphenyl, dimethylaminophenyl, methoxyphenyl, or cyanophenyl. In yet other embodiments, G is a para substituted phenyl. In still other embodiment, G is p-t-butylphenyl, p-dimethylaminophenyl, p-methoxyphenyl, or p-cyanophenyl.

In various embodiments of the compound, E is hydrogen. In other embodiments, E is G. In still other embodiments, E is —O-G. In yet other embodiments, E is —N(G)$_2$. In yet other embodiments, E is hydrogen, -G, —O-G, or —N(G)$_2$.

In various embodiments of the compound, A is -L$_A$-R$^1$, B is hydrogen, and C is hydrogen, and -L$_A$- is ethynyl or a bond. In some embodiments, A is -L$_A$-R$^1$, B is hydrogen, C is hydrogen, and -L$_A$- is a bond. In other embodiments, A is -L$_A$-R$^1$, B is hydrogen, C is hydrogen, and -L$_A$- is ethynyl. In yet other embodiments, A is -L$_A$-R$^1$, B is hydrogen, and C is -L$_C$-R$^1$, and -L$_A$- and -L$_C$- are bonds. In still other embodiments, A is -L$_A$-R$^1$, B is hydrogen, and C is -L$_C$-R$^1$, and -L$_A$- and -L$_C$- are ethynyl.

In various embodiments of the compound, the compound is a free base. In other embodiments, the compound is a salt. In still other embodiments, the compound is an inorganic salt. In yet other embodiments, the compound is an organometallic salt. In still other embodiments, the compound is a transition metal salt. In embodiments, the salt is a copper salt. In other embodiments, the salt is a zinc salt.

In some embodiments of the compound, E is halogen. In embodiments, the E may be bromo. In other embodiments, E is chloro. In still other embodiments, E is fluoro.

In some embodiments of the compound, the compound is
6-(anthracen-9-yl)-N-(pyridin-2-yl)pyridin-2-amine (1);
4-(10-((6-pyridin-2-ylamino)pyridin-2-yl)ethynyl)anthracen-9-yl)benzonitrile (2);
N-(anthracen-9-yl)-N-(pyridin-2-yl)pyridin-2-amine (3);
6-(anthracen-9-ylethynyl)-N-(pyridin-2-yl)pyridin-2-amine (4);
6-((10-(4-methoxyphenyl)anthracen-9-yl)ethynyl)-N-(pyridin-2-yl)pyridin-2-amine (5);
6-((10-(4-(dimethylamino)phenyl)anthracen-9-yl)ethynyl)-N-(pyridin-2-yl)pyridin-2-amine (6);
bis(6-(anthracen-9-ylethynyl)pyridin-2-yl)amine (7);
6-((10-(bis(4-tert-butylphenyl)amino)anthracen-9-yl)ethynyl)-N-(pyridin-2-yl)pyridin-2-amine (8);
6-((10-(bis(4-methoxyphenyl)amino)anthracen-9-yl)ethynyl)-N-(pyridin-2-yl)pyridin-2-amine (9); and
6-((10-bromoanthracen-9-yl)ethynyl)-N-(pyridin-2-yl)pyridin-2-amine;
or salts thereof.

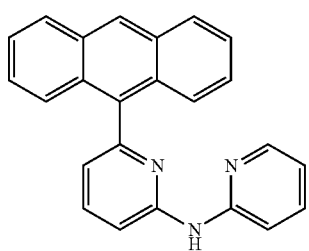

1

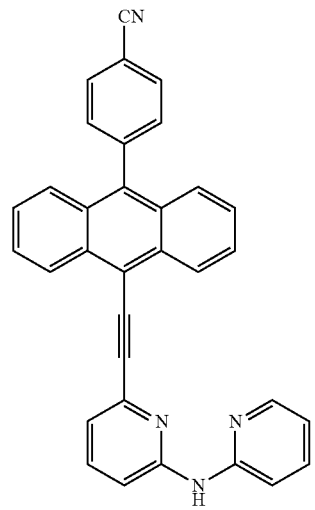

2

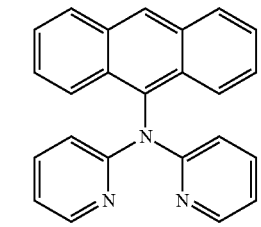

3

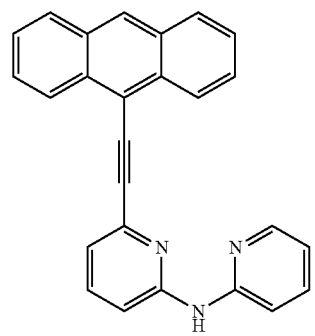

4

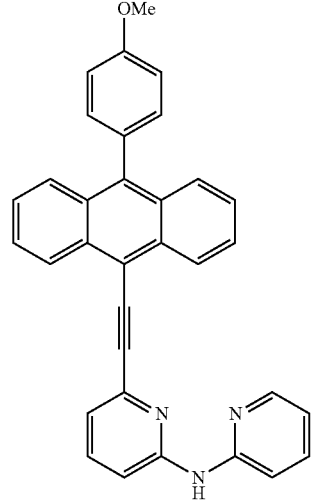

5

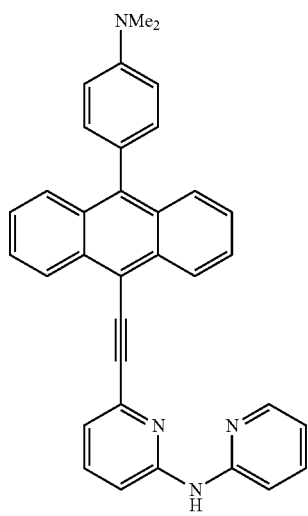

6

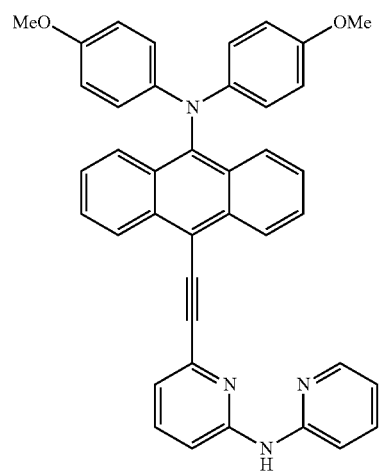

9

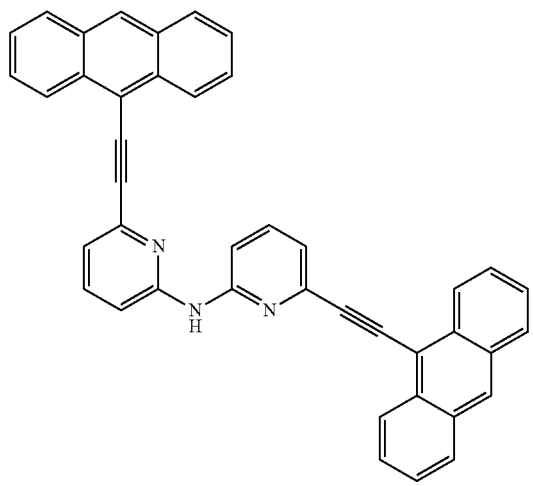

7

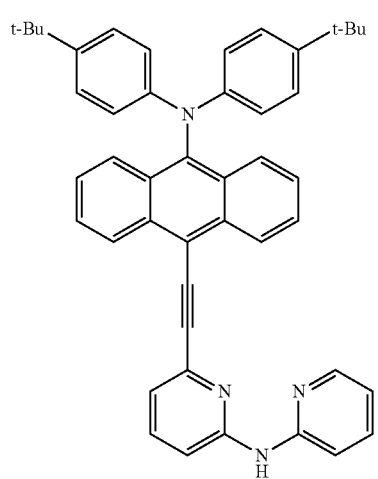

8

In embodiments of the compound, the compounds provide fluorescence, commonly in the visible spectrum, with high quantum yields. Fluorescence emission data is provided for compounds 1-9 are provided in Table 1. Normalized photoluminescence spectra are provided for compounds 1-9 in FIG. 1.

TABLE 1

| Compd. | $\lambda_{em}$ (nm) | $\Phi_F$ (quantum yields) (%) |
|---|---|---|
| 1 | 409 | 10 |
| 2 | 446 | 39 |
| 3 | 440 | 80 |
| 4 | 436 | 69 |
| 5 | 465 | 41 |
| 6 | 438 | 47 |
| 7 | 558 | 68 |
| 8 | 607 | 67 |
| 9 | 650 | 5 |

Dissociation temperatures of compounds 1-9 were obtained from TGA curves and presented in Table 2.

TABLE 2

| Compd. | 1 | 2 | 3 | 4 | 5 | 6 | 7 | 8 | 9 |
|---|---|---|---|---|---|---|---|---|---|
| $T_d$/° C. | 200 | 227 | 295 | 294 | 363 | 233 | 419 | 135 | 304 |

Embodiments include methods of preparing a compound of formula I:

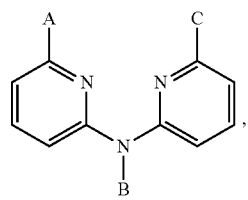

I wherein A is -L$_A$-R$^1$, B as hydrogen, and C as hydrogen. R$^1$ is

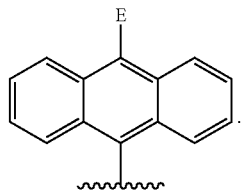

E is -G, and wherein G is an aryl, substituted aryl, heteroaryl, or substituted heteroaryl, the method comprising coupling 6-((10-bromoanthracen-9-yl)ethynyl)-N-(pyridin-2-yl)pyridin-2-amine with an arylboronate, substituted arylboronate, heteroarylboronate, or substituted heteroarylboronate.

Various embodiments of the method of preparation include wherein the aryl boronate is a dimethylaminophenylboronate. In other embodiments, the aryl boronate is an alkoxyphenylboronate. In still other embodiments, the aryl boronate is an aryl dimethoxyboronate. In yet another embodiment, the aryl boronate is an aryl thexylboronate. In still other embodiments, the coupling step comprises contacting the 6-((10-bromoanthracen-9-yl)ethynyl)-N-(pyridin-2-yl)pyridin-2-amine with an arylboronate, substituted arylboronate, heteroarylboronate, or substituted heteroarylboronate, with palladium tetrakis-triphenylphosphine and cesium carbonate in an aprotic solvent.

Embodiments include methods of preparing a compound of formula I:

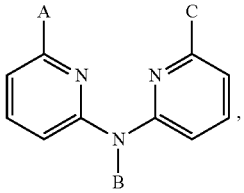

wherein A is -L$_A$-R$^1$, B is hydrogen, C is hydrogen, R$^1$ is

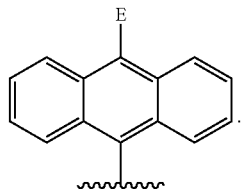

E is a hydrogen, halogen, -G, —O-G, or NG$_2$, and wherein G is an aryl, substituted aryl, heteroaryl, substituted heteroaryl, or alkyl, the method comprising coupling 6-ethynyl-2,2'-dipyridylamine with a 9-bromoanthracene compound. In some embodiments, the 9-bromoanthracene compound is 9-bromoanthracene. In other embodiments, wherein the 9-bromoanthracene compound is 10-p-methoxyphenoxy-9-bromoanthracene. In still other embodiments, the 9-bromoanthracene compound is 10-bis-(p-t-butylphenyl)-amino-9-bromoanthracene. In yet other embodiments, the 9-bromoanthracene compound is 10-bis-(p-methoxyphenyl)-amino-9-bromoanthracene. In various embodiments of the method of preparation, the coupling step comprises contacting the 6-ethynyl-2,2'-dipyridylamine with a 9-bromoanthracene compound in the presence of bis-triphenylphosphine palladium chloride and a cuprous salt. In other embodiments, the coupling comprises contacting the 6-ethynyl-2,2'-dipyridylamine with a 9-bromoanthracene compound in the presence of bis-triphenylphosphine palladium chloride, cuprous iodide, and an alkyl amine.

Embodiments include methods of detecting metal ions comprising detecting the wavelength of a compound of formula I:

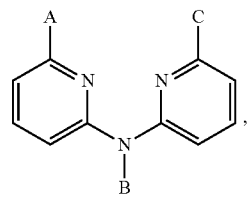

wherein A is hydrogen or -L$_A$-R$^1$, B is hydrogen or -L$_B$-R$^1$, C is hydrogen or -L$_C$-R$^1$, R$^1$ is

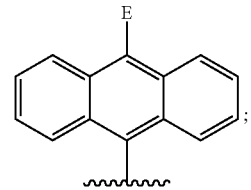

E is a hydrogen, halogen, -G, —O-G, or NG$_2$, wherein G is an aryl, substituted aryl, heteroaryl, substituted heteroaryl, or alkyl, wherein -L$_A$-, -L$_B$-, and -L$_C$- are independently a bond or ethynyl, at least one of A, B and C is -L$_A$-R$^1$, -L$_B$-R$^1$, or -L$_C$-R$^1$, and if B is -L$_B$-R$^1$ and -L$_B$- is a bond, then E is hydrogen, G, or —O-G. In some embodiments, the method comprises the steps of detecting the wavelength or spectral intensity of a compound, contacting the compound with a sample, determining a shift in the wavelength or change in spectral intensity.

Embodiments include detecting the visible wavelength and determining a shift in the visible spectrum in the presence of an ion. Some embodiments include a visual detection and visual determination. Other embodiments include using a spectrophotometer. In some embodiments, the shift in the visible spectrum is a red shift. In still other embodiments the shift is in the presence of divalent metal ion.

Still other embodiments include detecting a fluorescence wavelength and determining an intensity shift in the fluorescence in the presence of an ion. Some embodiments include a visual detection and visual determination of the intensity change. Other embodiments use a spectrophotometer. In some embodiments, the intensity change is a decrease in intensity. In still other embodiments the intensity change is in the presence of divalent metal ion.

Figure 2:
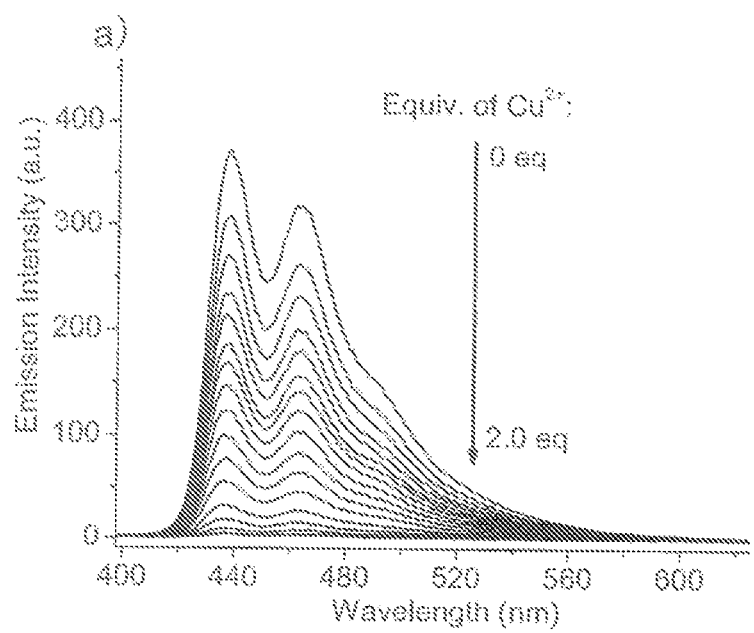
FIG. 2: A graph illustrating a change in emission intensity of a compound of FIG. 1 upon the addition of increasing amounts of Cu$^{2+}$ ion.

Embodiments provide methods employing compounds as described herein to detect metal ions. As an example, FIG. 2 shows the change in fluorescence emission intensity of 4-(10-((6-(pyridin-2-ylamino)pyridin-2-yl)ethynyl)anthracen-9-yl)benzonitrile (compound 2) with the addition of (0-2.0 equiv.) Cu$^{2+}$ in MeOH/H$_2$O (4/1, v/v) with $\lambda_{ex}$ fixed at 298 nm (one of the isosbestic points). The change in the luminescence upon coordination of metal ions may be useful for detection of gunpowder residue, bomb making activity, and/or environmental contamination such as heavy metal contamination of food or soil or water, as well as for detection of sites of meteor impact and even interplanetary exploration.

Figure 3:
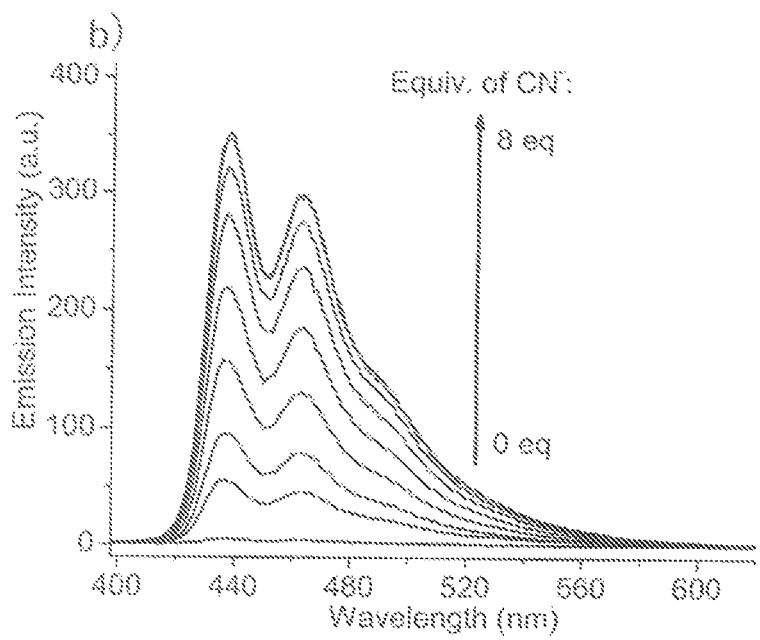
FIG. 3: A graph illustrating a change in emission intensity of the compound of FIG. 2 upon the addition of increasing amounts of cyanide ion.

The fluorescence emission reduction observed with compound 2 in the presence of cupric ion is reversible. Addition of cyanide ion effectively competes with compound 2 for chelation of the copper, and the fluorescence emission is restored (FIG. 3). The decrease and increase in intensity of the fluorescence may be repeated by addition of cupric ion and cyanide. FIG. 3 illustrates the fluorescence changes during titration of the compound 2-$Cu^{2+}$ complex (10 μM) with cyanide ion in MeOH/$H_2O$ (4/1, v/v), with $\lambda_{ex}$ fixed at 298 nm.

In another embodiment, a composition comprises a compound of general formula I as described herein and an organic polymer matrix. In embodiments, the composition may comprise a compound of general formula I, an organic polymer matrix and a solvent. Solvents include, but are not limited to, organic solvents such as toluene, diethyl ether, tetrahydrofuran, dichloromethane, and combinations thereof.

In yet another embodiment, a composition provides a fluorescent product or an electroluminescent product comprising a compound of general formula I as described herein. The product may be a flat panel display device. In a further embodiment is a composition providing an electroluminescent device for use with an applied voltage, comprising: a first electrode, an emitter which is an electroluminescent compound of general formula I as described herein, and a second, transparent electrode, wherein voltage is applied to the two electrodes to produce an electric field across the emitter so that the emitter electroluminesces. In a still further embodiment, a composition provides an electroluminescent device for use with an applied voltage, comprising: a first electrode, a second, transparent electrode, an electron transport layer adjacent the first electrode, a hole transport layer adjacent the second electrode, and an emitter which is an electroluminescent compound of general formula I interposed between the electron transport layer and the hole transport layer, wherein voltage is applied to the two electrodes to produce an electric field across the emitter so that the emitter electroluminesces.

Yet another embodiment is a method of producing electroluminescence, comprising the steps of: providing an electroluminescent compound of general formula I, as described herein, and applying a voltage across said compound so that said compound electroluminesces.

An advantage of preferred compounds is that they are highly soluble in common organic solvents such as toluene, diethyl ether, tetrahydrofuran, and dichloromethane. This permits the compounds to be blended easily and conveniently with organic polymer matrices. The role of the organic polymer matrix in such a mixture is at least two-fold. First, a polymer can provide protection for the compound from air degradation. Second, a polymer host matrix permits the use of a spin-coating or dip-coating process as a way to make films. Accordingly, embodiments include methods of applying compounds as described above to a surface. These methods include solvent cast from solution, electrochemical deposition, vacuum vapor deposition, chemical vapor deposition, spin coating and dip coating. The compounds may be applied alone or with a carrier. In some embodiments, they are applied in a composition including an organic polymer matrix.

Still another embodiment is a kit for detecting metal ions. The kit includes a solvent, a compound of formula I as described herein, and a mixing container. Solvents include, but are not limited to, organic solvents such as toluene, diethyl ether, tetrahydrofuran, dichloromethane, and combinations thereof. The solvent and the compound may be separate in the kit. The compound may be dissolved in the solvent in the kit. The kit may further contain standards of one or more inorganic ions. The kit is used by comparing the fluorescence and visible spectra of the compound in the solvent, mixing with a test sample, and detecting a change in intensity of the fluorescence or a shift in the visible spectrum. A comparison of the changes may be made to changes in fluorescence and visible spectra by using a standard with the compound in the solvent.

EXAMPLES

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples.

Novel luminescent compounds with emission colors that can be easily and systematically tuned to cover almost the entire visible spectral region were synthesized. In some embodiments, a dpa unit may be introduced to the 9-position of anthracene by a C—C bond or C—N bond to afford blue light emitting compounds. In other embodiments, the 9-position of anthracene may be linked to the 6-position of dpa by an ethynyl bridge. Such a connection mode can effectively extend the pi-conjugation systems and thus reduce the HOMO-LUMO energy gaps of the compounds, resulting in bathochromic shifts of the emission maxima. In these compounds, the electron deficient dpa unit may act as an electron acceptor. If electron donors are attached to the 10-position of anthracene, D-pi-A type luminescent materials may be developed.

Advantages of these compounds include: easy structural modification, tunable emission colors from violet (400 nm) to red (663 nm) by changing the connection mode between the two units as well as modulating the electron donors, high solid state quantum yields, good solubility and easy processing. Furthermore, the dpa unit in these compounds can be utilized to coordinate with metal ions to further modulate the emission wavelengths and intensities.

Example 1

Preparation of 1: 6-(anthracen-9-yl)-N-(pyridin-2-yl)pyridin-2-amine

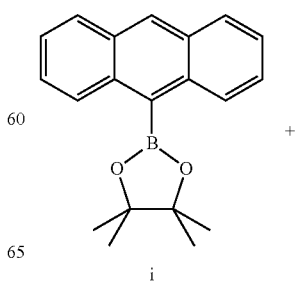

i

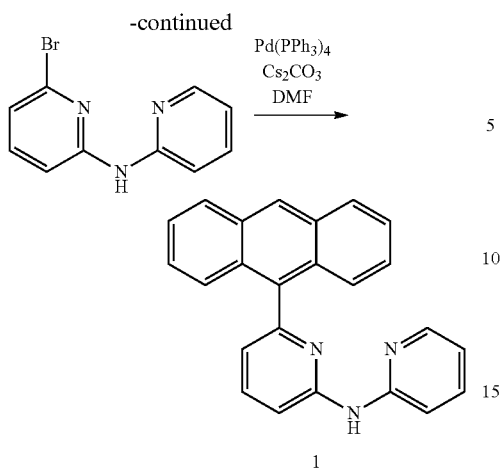

i (470 mg, 1.5 mmol), 6-bromo-2,2'-dpa (124 mg, 0.5 mmol), cesium carbonate (820 mg, 2.5 mmol), Pd(PPh$_3$)$_4$ (57 mg, 0.05 mmol) and DMF (15 mL) were placed in a Schlenk flask (100 mL), which was charged with nitrogen. The mixture was stirred at 85° C. for 24 hours. Then the mixture was dissolved in dichloromethane and washed with water, dried over anhydrous sodium sulfate, evaporated, and purified by a silica gel column to afford a yellow solid of 1 (10 mg, yield 6%), $\lambda_{em}$=409 (nm), $\Phi_F$=10% quantum yield.

Example 2

Preparation of 2: 4-(10-((6-(pyridin-2-ylamino)pyridin-2-yl)ethynyl)anthracen-9-yl)benzonitrile

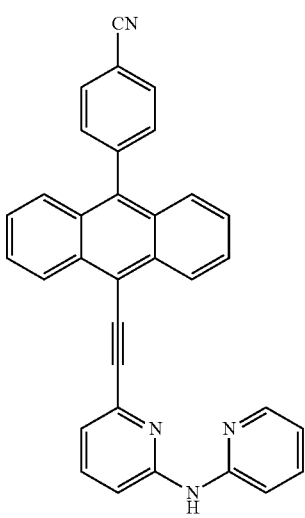

To a solution of 4-bromobenzonitrile (490 mg, 2.5 mmol) in dry tetrahydrofuran (20 mL) at −78° C., n-butyl lithium (1.4 mL, 0.58 mmol, 2.4 M in hexane) was added dropwise. The mixture was stirred at −78° C. for 1 hour. Then, trimethyl borate (0.5 mL) was added rapidly to the above solution and the resultant mixture was stirred for another 2 h. The resultant mixture was warmed up to room temperature and stirred overnight and the solution was then injected into a mixture of i1 (113 mg, 0.25 mmol), cesium carbonate (245 mg, 0.75 mmol), Pd(PPh$_3$)$_4$ (29 mg, 0.025 mmol), toluene (15 mL) and dimethylformamide (15 mL) in a Schlenk flask (100 mL), which was charged with nitrogen, and stirred at 85° C. for 24 hours. Then, the mixture was dissolved in dichloromethane and washed with water, dried over anhydrous sodium sulfate, evaporated, and purified by a silica gel column to afford the yellow solid (5 mg, yield 4%), $\lambda_{em}$=446 (nm), $\Phi_F$=39% quantum yield.

Example 3

Preparation of 3: N-(anthracen-9-yl)-N-(pyridin-2-yl)pyridin-2-amine

9-Bromoanthracene (3 g, 11.7 mmol), 2,2'-dpa (1.23 g, 7.2 mmol), copper sulfate (91 mg, 0.57 mmol), potassium carbonate (1.66 g, 12 mmol) and diphenyl ether (1.5 mL) were placed in a Schlenk flask (100 mL), which was charged with nitrogen. The mixture was stirred at 200° C. for 36 h, then directly purified by a silica gel column to afford a pale yellow solid (750 mg, yield 30%), $\lambda_{em}$=440 (nm), $\Phi_F$=80% quantum yield.

Example 4

Preparation of 4: 6-(anthracen-9-ylethynyl)-N-(pyridin-2-yl)pyridin-2-amine

9-Bromoanthracene (1.34 g, 5.2 mmol), 6-ethynyl-2,2'-dpa (0.6 g, 3.1 mmol), copper iodide (10 mg, 0.03 mmol), Pd(PPh$_3$)$_2$Cl$_2$ (216 mg, 0.05 mmol), diisopropylamine (12 mL) and tetrahydrofuran (48 mL) were placed in a Schlenk flask (250 mL), which was charged with nitrogen. The mixture was stirred at 70° C. for 15 hours. Then, the solvent was removed under reduced pressure, purified by a silica gel col-

Example 5

Preparation of 5: 6-((10-(4-methoxyphenyl)anthracen-9-yl)ethynyl)-N-(pyridin-2-yl)pyridin-2-amine

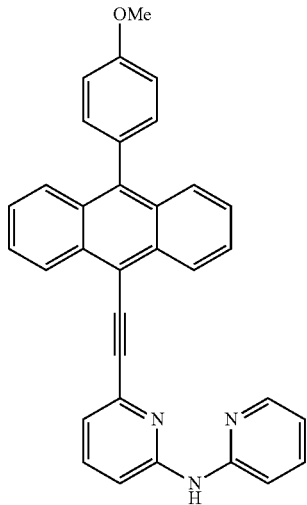

5 i1 (160 mg, 0.36 mmol), i2 (170 mg, 0.72 mmol), cesium carbonate (348 mg, 1.07 mmol), Pd(PPh$_3$)$_4$ (33 mg, 0.03 mmol) and DMF (15 mL) were placed in a Schlenk flask (100 mL), which was charged with nitrogen. The mixture was stirred at 85° C. for 14 hours. Then, the mixture was dissolved in dichloromethane and washed with water, dried over anhydrous sodium sulfate, evaporated, and purified by silica gel column to afford a yellow solid (18 mg, yield 10%), $\lambda_{em}$=465 (nm), $\Phi_F$=41% quantum yield.

Example 6

Preparation of 6: 6-((10-(4-(dimethylamino)phenyl)anthracen-9-yl)ethynyl)-N-(pyridin-2-yl)pyridin-2-amine

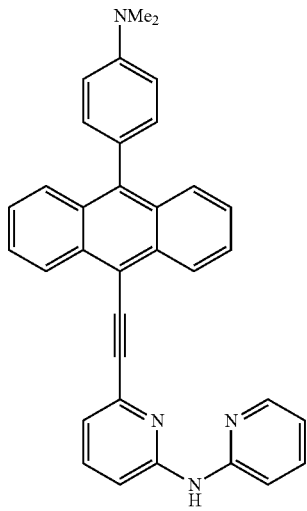

6 umn to afford a yellow solid (500 mg, yield 40%), $\lambda_{em}$=436 (nm), $\Phi_F$=69% quantum yield.

To a solution of 4-bromo-N,N-dimethylaniniline (500 mg, 2.5 mmol) in dry tetrahydrofuran (20 mL) at −78° C., n-butyl lithium (1.4 mL, 0.58 mmol, 2.4 M in hexane) was added dropwise. The mixture was stirred at −78° C. for 1 hour. Then, trimethyl borate (0.5 mL) was added rapidly to the above solution and the mixture was stirred for another 2 hour. The resultant mixture was warmed up to room temperature and stirred overnight and the solution was then injected into a mixture of i1 (113 mg, 0.25 mmol), cesium carbonate (245 mg, 0.75 mmol), Pd(PPh$_3$)$_4$ (29 mg, 0.025 mmol), toluene (15 mL) and DMF (15 mL) in a Schlenk flask (100 mL), which was charged with nitrogen, and stirred at 85° C. for 24 hours. Then, the mixture was dissolved in dichloromethane and washed with water, dried over anhydrous sodium sulfate, evaporated, and purified by a silica gel column to afford a yellow solid (20 mg, yield 16%), $\lambda_{em}$=438 (nm), $\Phi_F$=47% quantum yield.

Example 7

Preparation of 7: bis(6-(anthracen-9-ylethynyl)pyridin-2-yl)amine

7

9-Bromoanthracene (846 mg, 3.28 mmol), copper iodide (30 mg, 0.09 mmol), Pd(PPh$_3$)$_4$ (168 mg, 0.14 mmol), diisopropylamine (18 mL) and tetrahydrofuran (30 mL) were placed in a Schlenk flask (100 mL), which was charged with nitrogen. Then a solution of 6,6'-diethynyl-2,2'-dpa (0.3 g, 1.37 mmol) in tetrahydrofuran (5 mL) was injected in batches. The mixture was stirred at 70° C. for 21 hours. Then, the mixture was dissolved in dichloromethane and washed with water, dried over anhydrous sodium sulfate, evaporated, and purified by a silica gel column to afford a yellow solid (270 mg, yield 30%), $\lambda_{em}$=558 (nm), $\Phi_F$=68% quantum yield.

Example 8

Preparation of 8: 6-((10-(bis(4-tert-butylphenyl) amino)anthracen-9-yl)ethynyl)-N-(pyridin-2-yl)pyridin-2-amine

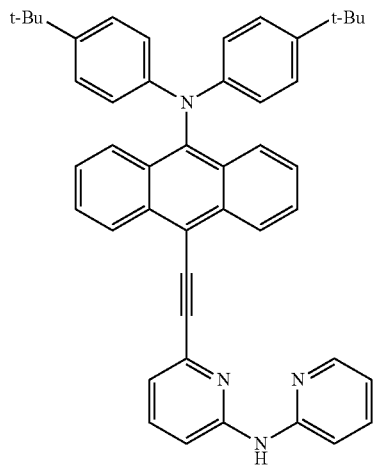

i3 (500 mg, 0.93 mmol), copper iodide (25 mg, 0.13 mmol), Pd(PPh$_3$)$_2$Cl$_2$ (90 mg, 0.13 mmol), diisopropylamine (7.5 mL) and tetrahydrofuran (25 mL) were placed in a Schlenk flask (100 mL), which was charged with nitrogen. Then a solution of 6-ethynyl-2,2'-dpa (0.38 g, 1.95 mmol) in tetrahydrofuran (10 mL) was injected in batches. The mixture was stirred at 70° C. for 33 hours. Then, the solvent was removed under reduced pressure, purified by a silica gel column to afford a yellow solid (170 mg, yield 28%), $\lambda_{em}$=607 (nm), $\Phi_F$=67% quantum yield.

Example 9

Preparation of 9: 6-((6-((10-(bis(4-methoxyphenyl) amino)anthracen-9-yl)ethynyl)-N-(pyridin-2-yl)pyridin-2-amine

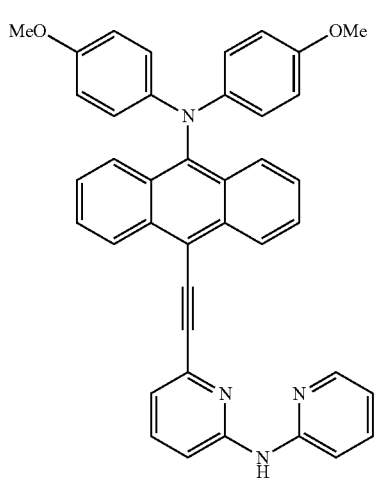

i4 (452 mg, 0.93 mmol), copper iodide (25 mg, 0.13 mmol), Pd(PPh$_3$)$_2$Cl$_2$ (90 mg, 0.13 mmol), diisopropylamine (7.5 mL) and tetrahydrofuran (25 mL) were placed in a Schlenk flask (100 mL), which was charged with nitrogen. Then a solution of 6-ethynyl-2,2'-dpa (365 mg, 1.87 mmol) in tetrahydrofuran (10 mL) was injected in batches. The mixture was stirred at 70° C. for 28 hours. Then, the solvent was removed under reduced pressure, and the residue was purified by a silica gel column to afford a red solid (103 mg, yield 18%), $\lambda_{em}$=650 (nm), $\Phi_F$=5% quantum yield.

Example 10

Fluorescence Probe of Compound 2, Showing Turn-On, Turn-Off Characteristics

When aqueous cuprate, 0-2.0 equiv. of Cu$^{2+}$, was added to a MeOH/H$_2$O solution of 2 (10 μM), as shown in FIG. 2, the fluorescence was almost completely quenched. This is due to the formation of non-fluorescent 2-Cu$^{2+}$ complex. Then, cyanide was added to the resulting solution. As shown in FIG. 3, a sharp fluorescence "turn on" was observed with the addition of 0-8.0 equiv. of CN$^-$. Thus, compound 2 can be used as a fluorescent "turn off" Cu$^{2+}$ probe with the detection limit of 9×10$^{-7}$ M and the 2-Cu$^{2+}$ ensemble can be used as a fluorescence "turn on" CN$^-$ probe with the detection limit of 2×10$^{-7}$ M. The fluorescence could be turned off and on repeatedly with the alternate addition of Cu$^{2+}$ and CN$^-$ ions, indicative of good reversibility of the probe.

Example 11

Fluorescent Compounds in Organic Light Emitting Diodes

NPB (4,4'-bis(N-(1-naphthyl-N-phenylamino)biphenyl) was used as a hole-transporting layer, BCP (2,9-dimethyl-4,7-diphenyl-1,10-phenanthroline) as an electron-transporting and hole-blocking layer, TPBi (1,3,5-tris(N-phenylbenzimidazol-2-yl)benzene) or Alq$_3$ as an electron-transporting layer, LiF/Al as a cathode, and ITO acts as anode. Device with the structure of ITO/NPB/emitter/BCP/TPBi (or Alq$_3$)/LiF/Al was fabricated by sequential vacuum deposition of organic materials, LiF, and Al on pre-treated ITO. In the device, any one of the compounds selected from compounds 1-9 can be used as the host emitter.

Example 12

Fluorescent Compounds as Fluorescent Dyes

Compounds 1-9 can be used as fluorescent dyes with the advantages of high quantum yields, good thermostability, and easily modulated colors. Fluorescent dyes can be used for fabricating fluorescent paint for roadway signs, luminaire posts, and fluorescent clothing, etc. For example, green color is very striking in the dark, compound 7 can be used as green dyes for making fluorescent clothes, which can be used by traffic police in the law enforcement processes.

What is claimed is:

1. A luminescent compound of formula I,

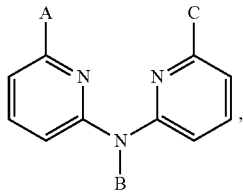

A is hydrogen or -$L_A$-$R^1$;
B is hydrogen or -$L_B$-$R^1$;
C is hydrogen or -$L_C$-$R^1$;
wherein $R^1$ is

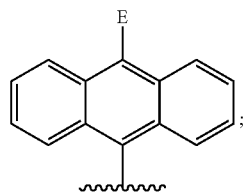

E is a hydrogen, halogen, -G, —O-G, or $NG_2$;
G is an aryl, substituted aryl, heteroaryl, substituted heteroaryl, or alkyl;
wherein -$L_A$-, -$L_B$-, and -$L_C$- are independently a bond or ethynyl;
at least one of A, B and C is -$L_A$-$R^1$, -$L_B$-$R^1$, or -$L_C$-$R^1$;
if B is -$L_B$-$R^1$ and -$L_B$- is a bond, then E is hydrogen, G, or —O-G;
and salts thereof.

2. The compound of claim 1, wherein G is phenyl, substituted phenyl, biphenyl, substituted biphenyl, pyridyl, substituted pyridyl, naphthyl, substituted naphthyl, quinolyl, substituted quinolyl, isoquinolyl, substituted isoquinolyl, fluorenyl, substituted fluorenyl, terphenyl, substituted terphenyl, methyl, ethyl, propyl, isopropyl, or t-butyl.

3. The compound of claim 1, wherein G is phenyl, biphenyl, pyridyl, naphthyl, quinolyl, isoquinolyl, fluorenyl or terphenyl.

4. The compound of claim 1, wherein G is phenyl.

5. The compound of claim 1, wherein G is 2-pyridyl.

6. The compound of claim 1, wherein G is methyl, ethyl, propyl, isopropyl, or t-butyl.

7. The compound of claim 1, wherein A is -$L_A$-$R^1$ and -$L_A$- is a bond; B is hydrogen; and C is hydrogen.

8. The compound of claim 1, wherein B is -$L_B$-$R^1$ and -$L_B$- is a bond; A is hydrogen; and C is hydrogen.

9. The compound of claim 1, wherein A is -$L_A$-$R^1$ and -$L_A$- is ethynyl; B is hydrogen; and C is hydrogen.

10. The compound of claim 1, wherein substitution on G is one or more of alkyl, aryl, alkoxy, alkylamino, halogen, aryloxy, arylamino, alkylsilyl, or arylsilyl.

11. The compound of claim 1, wherein substitution on G is t-butylphenyl, dimethylaminophenyl, methoxyphenyl, or cyanophenyl.

12. The compound of claim 1, wherein G is a para substituted phenyl.

13. The compound of claim 1, wherein G is p-t-butylphenyl, p-dimethylaminophenyl, p-methoxyphenyl, or p-cyanophenyl.

14. The compound of claim 1, wherein E is hydrogen.

15. The compound of claim 1, wherein E is G.

16. The compound of claim 1, wherein E is —O-G.

17. The compound of claim 1, wherein E is —$N(G)_2$.

18. The compound of claim 1, wherein A is -$L_A$-$R^1$, B is hydrogen, C is hydrogen.

19. The compound of claim 1, wherein A is -$L_A$-$R^1$, B is hydrogen, and C is -$L_C$-$R^1$ and -$L_A$- and -$L_C$- are bonds.

20. The compound of claim 1, wherein A is -$L_A$-$R^1$, B is hydrogen, C is -$L_C$-$R^1$, and -$L_A$- and -$L_C$- are ethynyl.

21. The compound of claim 1, wherein the compound is a salt.

22. The compound of claim 1, wherein E is halogen.

23. The compound of claim 1, wherein E is bromo.

24. The compound of claim 1, wherein the compound is:
6-(anthracen-9-yl)-N-(pyridin-2-yl)pyridin-2-amine;
4-(10-(((6-(pyridin-2-ylamino)pyridin-2-yl)ethynyl)anthracen-9-yl)benzonitrile;
N-(anthracen-9-yl)-N-(pyridin-2-yl)pyridin-2-amine;
6-(anthracen-9-ylethynyl)-N-(pyridin-2-yl)pyridin-2-amine;
6-((10-(4-methoxyphenyl)anthracen-9-yl)ethynyl)-N-(pyridin-2-yl)pyridin-2-amine;
6-((10-(4-(dimethylamino)phenyl)anthracen-9-yl)ethynyl)-N-(pyridin-2-yl)pyridin-2-amine;
bis(6-(anthracen-9-ylethynyl)pyridin-2-yl)amine;
6-((10-(bis(4-tert-butylphenyl)amino)anthracen-9-yl)ethynyl)-N-(pyridin-2-yl)pyridin-2-amine;
6-((10-(bis(4-methoxyphenyl)amino)anthracen-9-yl)ethynyl)-N-(pyridin-2-yl)pyridin-2-amine; and
6-((10-bromoanthracen-9-yl)ethynyl)-N-(pyridin-2-yl)pyridin-2-amine;
or salts thereof.

* * * * *